(12) United States Patent
Momberg et al.

(10) Patent No.: US 9,492,548 B2
(45) Date of Patent: Nov. 15, 2016

(54) EMULSION CONTAINING A NON-LIVE MEDICINAL SUBSTANCE

(71) Applicant: Intervet Inc., Summit, NJ (US)

(72) Inventors: Erwin Momberg, Cuyjk (NL);
Theodorus Jansen, Venray (NL);
Henricus Johannes Maria Jagt, Venlo (NL)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 14/102,575

(22) Filed: Dec. 11, 2013

(65) Prior Publication Data

US 2014/0170185 A1    Jun. 19, 2014

(30) Foreign Application Priority Data

Dec. 14, 2012   (EP) .................................... 12197191

(51) Int. Cl.
| | |
|---|---|
| *A61K 47/36* | (2006.01) |
| *A61K 38/02* | (2006.01) |
| *A61K 39/17* | (2006.01) |
| *A61K 39/12* | (2006.01) |
| *A61K 39/155* | (2006.01) |
| *A61K 39/215* | (2006.01) |
| *A61K 39/00* | (2006.01) |

(52) U.S. Cl.
CPC ............... *A61K 47/36* (2013.01); *A61K 38/02* (2013.01); *A61K 39/12* (2013.01); *A61K 39/155* (2013.01); *A61K 39/17* (2013.01); *A61K 39/215* (2013.01); *A61K 2039/5252* (2013.01); *A61K 2039/552* (2013.01); *A61K 2039/55566* (2013.01); *A61K 2039/575* (2013.01); *C12N 2760/18134* (2013.01); *C12N 2770/20034* (2013.01)

(58) Field of Classification Search
None
See application file for complete search history.

(56) References Cited

U.S. PATENT DOCUMENTS 4,481,188 A  * 11/1984 Apontoweil et al. ...... 424/222.1
6,190,700 B1 *  2/2001 Okada et al. ................ 424/499

FOREIGN PATENT DOCUMENTS

| CN | 101716150 | * | 6/2010 |
|---|---|---|---|
| EP | 0 556 394 A1 | | 8/1993 |
| EP | 0 599 543 A1 | | 6/1994 |
| EP | 1 550 453 A1 | | 7/2005 |
| EP | 2 462 950 A1 | | 6/2012 |

OTHER PUBLICATIONS

Perez-Rodriguez et al. (Journal of Controlled Release. 2003; 89: 71-85).*
Yuan et al. (Pharmaceutical Research. 2010; 27: 1285-1295).*
Cornacchia et al. (Food Biophysics. Published online: Dec. 23, 2011; 7:93-101).*
Lee et al. (Journal of Biological Chemistry. 1981; 256 (14): 7193-7201).*
European Search Report for EP Application No. EP 12 19 7191, dated May 6, 2013.

* cited by examiner

Primary Examiner — Shanon A Foley

(57) ABSTRACT

The present invention pertains to an emulsion comprising an aqueous phase and an oily phase, the aqueous phase containing a non-live medicinal substance, wherein the aqueous phase comprises at least 30% w/w sugar. The invention also pertains to a method to shield a medicinal substance present in an aqueous phase emulsified with an oily phase, from interaction with the oily phase, and to a vaccine comprising as an antigen a killed micro-organism or a subunit of a micro-organism, the antigen being present in an aqueous phase that is dispersed in an oily phase, wherein the aqueous phase comprises at least 30% w/w sugar.

20 Claims, No Drawings

EMULSION CONTAINING A NON-LIVE MEDICINAL SUBSTANCE

BACKGROUND OF THE INVENTION

The present invention pertains to an emulsion comprising an aqueous phase and an oily phase, the aqueous phase containing a non-live medicinal substance. The invention also pertains to a method to shield a medicinal substance present in an aqueous phase emulsified with an oily phase, from interaction with the oily phase, and to a vaccine comprising as an antigen a killed micro-organism or a subunit of a micro-organism, the antigen being present in the aqueous phase of the emulsion.

Aqueous compositions containing a non-live medicinal substance are commonly known in the art of medicine. They may be used as such, for example as a spray or formulation for oral administration. Stability of the medicinal substance is in most cases not a problem when compared to live medicinal substances such as live micro-organisms. In general, chemical decay in water is for most non-live substances easy to control for example by storing the composition at low temperatures (2-8° C.) and by shielding from the impact of UV radiation (typically by storing the compositions in a regular refrigerator). Also, aqueous formulations in general have no safety problems associated with the carrier fluid since water does not evoke any adverse reactions upon administration, either locally (for example via the mouth) or systemically (for example intra-muscular or via topical application). For some applications however, the presence of an oily phase is preferred, for example to stimulate the effectiveness of the medicinal substance (for example the use of an adjuvant oil in case the medicinal substance is an antigen), or to create better bioavailability (for example the use of an oil to create more effective topical application). Therefore, in the art it is common to create an emulsion of the aqueous phase containing the medicinal substance and an oily phase.

SUMMARY OF THE INVENTION

It is applicant's recognition that the use of such an emulsion may be disadvantageous for the effectiveness of the medicinal substance present in the aqueous phase. In such an emulsion namely, there is a huge surface where the aqueous phase and oily phase or constituents thereof may interact, possibly decreasing the effectiveness of the medicinal substance. In particular when using a non-inert medicinal substance such as a biologic molecule or inactivated (killed) micro-organism, possibly in conjunction with a non-inert oil such as a metabolisable oil, the negative impact of the presence of the oil may be substantial. But also when using inert oils, the presence of the oil may be disadvantageous, for example since the medicinal substance may tend to either concentrate at the surface between the two phases, or leak into the oily phase, or interact with additives in oil phase etc.

It is an object of the present invention to provide an improved emulsion that at least mitigates the problems that may arise due to interaction of the medicinal substance with the oily phase. To this end an emulsion according to the preamble has been devised, wherein the aqueous phase comprises at least 30% w/w sugar. Surprisingly it has been shown that by adding a large amount of sugar, a possible interaction between the medicinal substance and constituents of the oily phase may be decreased or even prevented. Beforehand it was expected that by adding sugar to the aqueous phase, which process inherently decreases the polarity of the aqueous phase, the interaction between the aqueous phase and the oily phase would increase. However, contrary to the expectation it appears that the medicinal substance can be shielded from a negative impact that results from interaction with (constituents present in) the oily phase. Next to this, it was surprisingly observed that there are no safety problems with this new emulsion, even upon intramuscular administration despite the presence of a potentially immunogenic sugar at a very high concentration.

The present invention is highly advantageous in the art of non-live vaccines (typically containing an inactivated micro-organism or a subunit of a micro-organism as an antigen), wherein the efficacy of the vaccine commonly relies on the presence of an oily phase as an adjuvant. Typical adjuvant oils are fatty acid ethyl esters (FAEE), Drakeol6 (available from Calumet Penreco, USA), cotton seed oil, ISA763A and ISA50 (both available from Seppic, France), squalane, squalene, Marcol® 52 (available from Exxon Chemicals, USA), alpha tocopheryl acetate, Miglyol 840 (Huls, Germany). The present invention may improve the stability of the vaccine by shielding the antigen from interaction with the oily phase. In general, a vaccine can be manufactured by using art-known methods that basically comprise admixing the antigens (or a composition containing the antigens) with a pharmaceutically acceptable carrier, e.g. a liquid carrier such as (optionally buffered) water. Optionally other substances such as protectants, viscosity modifiers or other components are added depending on the intended use or required properties of the vaccine.

It is noted that for a living medicinal substance such as a live attenuated bacterium or virus, sugar is commonly known as a stabilizer to create an environment wherein the micro-organism has a higher survival rate than without the stabilizer being present. However, stabilization of a live micro-organism is a completely different process than shielding a non-live substance from interaction with an oily phase. The problem that may arise when a non-live medicinal substance interacts with an oily phase in an emulsion of the aqueous carrier of the substance and the oily phase, is not even related to the problem of creating an environment wherein a live micro-organism survives.

DEFINITIONS

An emulsion: a dispersed system of two immiscible liquid phases, wherein an emulsifying agent is present that stabilizes the liquid-liquid interface. Typically the dispersed phase comprises droplets between 0.05 and 100 µm. An emulsifying agent is typically a surface active agent (often a detergent or surfactant), but may also be a compound comprising colloidal particles. Also, microscopic air bubbles have been described as emulsifying agent.

A non-live medicinal substance: a substance that is not able to (self-)replicate by an essentially biological process and can be used to prevent, treat or cure a disease or disorder of a living animal, in particular a human being or non-human animal. Typical non-live medicinal substances are small molecules, biological molecules such as antibodies, proteins, polysaccharides and inactivated micro-organisms (typically killed bacteria or viruses).

Aqueous: freely miscible with water at room temperature, i.e. being miscible such that a stable homogenous phase can be formed.

An oil: a substance being liquid at room temperature and atmospheric pressure, which liquid is not freely miscible with water.

An aqueous phase: a phase based essentially on water as a carrier medium or another aqueous solvent, or a mixture of water and one or more aqueous solvents.

An oily phase: a phase based essentially on an oil or a mixture of oils as carrier medium.

A sugar: any of a group of water-soluble carbohydrates of relatively low molecular weight and typically having a sweet taste. The term "sugar" includes reducing sugars (such as fructose and maltose), non-reducing sugars (such as sucrose and trehalose), sugar alcohols (such as xylitol and sorbitol), sugar acids (such as gluconic acid and tartaric acid) and mixtures thereof.

Inert: in essence not being chemically reactive under ordinary conditions (i.e. normal pressure and room temperature), thus lacking any substantial participation in chemical reactions. Typically, a large amount of (activation) energy is required to drive such reactions, usually in the form of heat, pressure, radiation, etc. often assisted by catalysts.

A non polymeric sugar: mono-, di-, tri-, and oligomeric sugar molecules, comprising at most six monomeric sugar molecules.

A biologically active protein: any protein that has a three-dimensional structure such that the protein is able to induce or interfere with a physiological process in a living organism, such as a metabolic process or an immunological process. The term biologically active protein may denote a full-length protein or a fragment thereof. Examples of biologically active proteins are enzymes, toxins, toxoids, any (other) immunological protein (for example a surface protein of a micro-organism or a fragment thereof), an antibody or a fragment thereof etc. Vaccines typically contain one or more biologically active proteins, either as part of a living or killed micro-organism, or as an isolated or recombinantly expressed subunit of such a micro-organism.

Metabolisable: being degradable by an animal after administration to that animal using in essence one or more of its metabolic processes.

% w/w: percentage mass over total mass.

A vaccine: a constitution suitable for application to an animal, comprising one or more antigens in an immunologically effective amount (i.e. capable of stimulating the immune system of the target animal sufficiently to at least reduce the negative effects of a challenge of the wild-type micro-organisms), which upon administration to the animal induces an immune response for treating a disease or disorder, i.e. aiding in preventing, ameliorating or curing the disease or disorder.

EMBODIMENTS OF THE INVENTION

In a first embodiment the medicinal substance comprises a biologically active protein. Although in the art it is commonly assumed that biologically active proteins, since they are non-live, are reasonably stable, applicant recognised that when present in an aqueous phase that is constituted with an oily phase to be part of an emulsion, a negative impact on the efficacy of the protein may occur. The present invention appears to be particularly suitable to shield biologically active proteins from such a negative impact and hence improve the freedom of use of these medicinal substances. For example, they may be stored for a prolonged period, or stored at a higher temperature or be brought over to any other environment where there is a possible impact on their efficacy, without substantially losing the latter or at least maintaining it substantially better when compared with a formulation wherein the aqueous phase does not comprise at least 30% w/w of sugar.

In another embodiment, the medicinal substance comprises a killed micro-organism.

Since a killed micro-organism is in fact a constitution comprising multiple biologically active proteins, applicant recognised that the present invention may be used advantageously for this type of medicinal substance. In particular, applicant found that the present invention may substantially impact the efficacy of a constitution wherein the killed micro-organism is an inactivated enveloped virus, in particular infectious bronchitus virus or Newcastle disease virus.

In yet another embodiment the aqueous phase is dispersed in the oily phase. For example, the emulsion is of the W/O ("water-in-oil") type. The latter emulsion has the advantage of being able to have a low viscosity, despite the fact that the aqueous phase contains a very high amount of sugar which inherently makes the aqueous phase itself (very) syrupy.

In an embodiment the oily phase contains a non-inert oil. A non-inert oil (although being in principal less stable than an inert oil and thus may react with other constituents present in the emulsion) may be advantageously used in an emulsion according to the invention since the potential negative impact of the non-inertness needs to have no substantial influence on the efficacy of the medicinal substance. This greatly improves the freedom to use other oils than inert oils, even when the medicinal substance is prone to chemical degradation under influence of the oil.

In another embodiment the oily phase contains a metabolisable oil, such as for example a fatty acid ethyl ester oil (FAEE), cotton seed oil, tung oil, squalane, squalene, alpha tocopheryl acetate and Miglyol. A metabolisable oil has the inherent advantage of being biologically degradable by the animal to which the emulsion is administered. However, a metabolisable oil also has the disadvantage of being chemically reactive per se.

Therefore, although commonly mentioned in literature for several decades, actual application of such oils in an emulsion containing a non-live medicinal substance for administration to animals is not widespread. The present invention overcomes the downside of using such a metabolisable oil with respect to a potential negative impact on the medicinal substance. In an embodiment, the oily phase contains an ester oil, i.e. an oil of which the constituting molecules are ester molecules. Typical ester oils are ethyl-esters and triglyceride esters of fatty acids.

In yet another embodiment the sugar contains a non-polymeric sugar. A non-polymeric sugar is believed to be capable of directly interacting with the non-live medicinal substance, in particular when this substance comprises a biologically active protein, to provide for an additional effect next to the shielding from the oil.

In an embodiment the sugar is chosen from the group consisting of sucrose, saccharose, sorbitol, mannitol, trehalose, maltose, maltodextrin and/or mixtures thereof.

It is believed that a content of sugar even higher than 30% w/w is better for application in the emulsion of the present invention. Therefore, preferably the aqueous phase comprises at least 40% w/w of sugar, preferably at least 50% w/w of sugar, more preferably at least 60% w/w of sugar.

The present invention in particular describes the use of IB or ND inactivated viruses, in an emulsion stabilized by the presence of sorbitol.

Examples

Emulsions were made having an aqueous phase, dispersed in an oily phase and stabilised with surfactant. The aqueous phase contains inactivated virus as the non-live medicinal substance. The virus was harvested from the allantois fluid from chicken eggs. The resulting aqueous phase typically contains about 40-50% allantois fluid next to water (WFI). Various viruses are used, infectious bronchitus virus strain m41 (IB-1), infectious bronchitus virus strain D274 (IB-2) and Newcastle disease virus clone 30 (ND). These are the same antigens as present in the product "Nobilis IB multi+ND" (available from MSD Animal Health).

The first type of emulsion is based on the mineral oil Marcol® 52 (available from ExxonMobil) and the surfactants Tween® 80 and Span® 80 (both available from Sigma Aldrich). The ratio between the aqueous phase and the oily phase is 1:1. This type of emulsion is commonly used in commercially available vaccines such as Nobilis IB+ND as available from MSD Animal Health). The second type of emulsion is based on the metabolisable ester oils alpha tocopheryl actetate and ethyl oleate (in the mass ratio 1:6.33) and the surfactant Cithrol DPHS (available from Croda International). The ratio between the aqueous phase and the oily phase is 1:1.5. The following formulations were made using a common Ultra-Turrax® mixer to emulsify a mixture of the constituents:

TABLE 1

Emulsion types

| Emulsion No | Oily phase | Antigen | Aqueous phase |
|---|---|---|---|
| 1 | Marcol ® 52 | IB-1 | WFI, allantois fluid |
| 2 | Marcol ® 52 | IB-2 | WFI, allantois fluid |
| 3 | Marcol ® 52 | ND | WFI, allantois fluid |
| 4 | Ester oil | IB-1 | WFI, allantois fluid |
| 5 | Ester oil | IB-2 | WFI, allantois fluid |
| 6 | Ester oil | ND | WFI, allantois fluid |
| 7 | Ester oil | IB-1 | WFI, allantois fluid, 30.6% sorbitol w/w |
| 8 | Ester oil | ND | WFI, allantois fluid, 30.6% sorbitol w/w |

The formulations 7 and 8 contain 30.6% sorbitol w/w in the aqueous phase, viz. this phase contains per 100 grams in total, 30.6 grams sorbitol. In order to be able and arrive at higher sugar concentrations, the allantois fluid may be concentrated to obtain up till for example a ten time increase in antigen concentration. This way, the aqueous phase could be constituted by using about 95% of water and 5% of allantois fluid, the water being used as the carrier to add the sugar. This way, mass percentages of sugar up till about 70-75% can be reached depending on the type of sugar.

In a first series of experiments, the formulations 1 through 6 were tested for immunogenic efficacy in SPF chickens after storage at 2-8° C. for 0, 6 or 12 months. For this, 3-4 week-old White Leghorn chickens were assigned to groups of 10 chickens each. For the IB vaccines, the chickens received 0.5 ml of the vaccine, administered via the intramuscular route in the thigh muscle. For the ND vaccine the same route was chosen, albeit that the dose was 0.01 ml.

At six weeks post vaccination blood samples were taken from the wing vein of each chicken. In each sample the titre against the antigen was determined. Within each group, the mean of the titres was established. The results for the Marcol® based emulsions are indicated in Table 2. The results for the ester oil emulsions are indicated in Table 3.

TABLE 2 titre against antigen in a Marcol ® based emulsion after storage

| | t = 0 | | t = 6 months | | t = 12 months | |
|---|---|---|---|---|---|---|
| Emulsion No | log10 | (std) | log10 | (std) | log10 | (std) |
| 1 | 5.0 | (1.1) | 5.3 | (1.0) | 5.8 | (1.5) |
| 2 | 6.0 | (1.0) | 5.9 | (1.3) | 6.7 | (1.3) |
| 3 | 6.4 | (1.3) | 6.0 | (0.5) | 6.6 | (0.7) |

TABLE 3 titre against antigen in an ester oil based emulsion after storage

| | t = 0 | | t = 6 months | | t = 12 months | |
|---|---|---|---|---|---|---|
| Emulsion No | log10 | (std) | log10 | (std) | log10 | (std) |
| 4 | 5.2 | (1.5) | 4.2 | (0.6) | 4.1 | (0.3) |
| 5 | 5.6 | (0.8) | 4.4 | (1.0) | 4.2 | (0.6) |
| 6 | 6.5 | (1.0) | 3.6 | (1.2) | 3.9 | (0.9) |

As can be seen, the titres in the ester oil based emulsion are negatively impacted by storage for all three types of antigens. In order to at least mitigate this negative influence, the same emulsion types as in formulations 4 and 6 were tested, but with 30.6% of sorbitol in the aqueous phase, viz. formulations 7 and 8. These formulations were made aiming at a starting titre of between 8.0 and 9.0 at a full dose of 0.5 ml for both types of antigen. These vaccines were stored during 17 months and regularly tested as indicated above, albeit that in all case 0.5 ml of the formulations were being used to be able and compare the data with the starting value of between 8.0 and 9.0 for the full dose of 0.5 ml. The emulsion appeared to induce no safety problems and had a viscosity enabling administration using a standard manually operated syringe. The results for the titres are indicated in table 4.

TABLE 4 titre in an ester oil based emulsion with 30.6% sorbitol in the aqueous phase

| Emulsion No | t = 0 log10 | t = 7 months log10 | t = 14 months log10 | t = 17 months log10 |
|---|---|---|---|---|
| 7 | 8-9.0 | 8.6 | 9.0 | 9.0 |
| 8 | 8-9.0 | 9.6 | 9.7 | 9.5 |

As can be seen, the presence of the sugar in the aqueous phase completely overcomes the negative influence of the ester oil during storage. The titres remained at the level of formulation for at least 17 months.

The invention claimed is:

1. A vaccine comprising an emulsion comprising an aqueous phase and an oily phase, wherein the aqueous phase contains a non-live medicinal substance, and wherein the aqueous phase comprises at least 30% w/w sugar; wherein the non-live medicinal substance is an inactivated micro-organism or a subunit of a micro-organism; wherein the vaccine has a titer; and wherein the titer of the vaccine remains at the same level for at least 17 months of storage at 2-8° C.

2. The vaccine of claim 1, wherein the medicinal substance comprises a biologically active protein.

3. The vaccine of claim 1, wherein the medicinal substance comprises an inactivated micro-organism.

4. The vaccine of claim 3, wherein the killed micro-organism is an inactivated enveloped virus.

5. The vaccine of claim 4, wherein the enveloped virus is infectious bronchitus virus or Newcastle disease virus.

6. The vaccine of claim 1, wherein the aqueous phase is dispersed in the oily phase.

7. The vaccine emulsion of claim 1, wherein the emulsion is of the W/O type.

8. The vaccine of claim 1, wherein the oily phase contains a non-inert oil.

9. The vaccine of claim 1, wherein the oily phase contains a metabolisable oil.

10. The vaccine of claim 1, wherein the oily phase contains an ester oil.

11. The vaccine of claim 1, wherein the sugar contains a non-polymeric sugar.

12. The vaccine of claim 1, wherein the sugar is chosen from the group consisting of sucrose, saccharose, sorbitol, mannitol, trehalose, maltose and maltodextrin or mixtures thereof.

13. The vaccine of claim 1, wherein the aqueous phase comprises at least 40% w/w of sugar.

14. A method to shield a medicinal substance present in an aqueous phase emulsified with an oily phase in a vaccine from interaction with the oily phase by formulating the aqueous phase to contain at least 30% w/w sugar; wherein the non-live medicinal substance is an inactivated micro-organism or a subunit of a micro-organism.

15. The vaccine of claim 13, wherein the aqueous phase comprises at least 50% w/w of sugar.

16. The vaccine of claim 13, wherein the aqueous phase comprises at least 60% w/w of sugar.

17. The vaccine of claim 12, wherein the sugar is sorbitol.

18. The vaccine of claim 17, wherein the oily phase comprises alpha tocopheryl acetate and ethyl oleate.

19. The method of claim 14 wherein the sugar is sorbitol and the oily phase comprises alpha tocopheryl acetate and ethyl oleate.

20. The method of claim 19 wherein the medicinal substance comprises an inactivated enveloped virus.

* * * * *